United States Patent
Fabrice et al.

(10) Patent No.: US 7,361,781 B2
(45) Date of Patent: Apr. 22, 2008

(54) PROCESS FOR THE PREPARATION OF 2,3,5-TRIMETHYLHYDROQUINONE DIACYLATES

(75) Inventors: Aquino Fabrice, Reiningue (FR); Bonrath Werner, Freiburg (DE); Pace Francesco, Rheinfelden (CH)

(73) Assignee: DSM IP Assets B.V., TE Heerlen (NL)

( * ) Notice: Subject to any disclaimer, the term of this patent is extended or adjusted under 35 U.S.C. 154(b) by 0 days.

(21) Appl. No.: 10/576,324

(22) PCT Filed: Oct. 26, 2004

(86) PCT No.: PCT/EP2004/012058

§ 371 (c)(1),
(2), (4) Date: Sep. 21, 2006

(87) PCT Pub. No.: WO2005/044775

PCT Pub. Date: May 19, 2005

(65) Prior Publication Data

US 2007/0123720 A1    May 31, 2007

(30) Foreign Application Priority Data

Nov. 7, 2003 (EP) .................................. 03025513

(51) Int. Cl.
C07C 67/02 (2006.01)
(52) U.S. Cl. ..................................... 560/254

(58) Field of Classification Search ..................... None
See application file for complete search history.

(56) References Cited

U.S. PATENT DOCUMENTS

| | | | |
|---|---|---|---|
| 3,053,884 A | | 9/1962 | Touey et al. |
| 3,920,582 A | * | 11/1975 | Rona ........................... 502/168 |
| 5,908,956 A | * | 6/1999 | Takahashi et al. ............ 560/79 |
| 6,103,924 A | | 8/2000 | Shi et al. |
| 2002/0004619 A1 | | 1/2002 | Krill et al. |

FOREIGN PATENT DOCUMENTS

| | | |
|---|---|---|
| DE | 21 49 159 | 4/1972 |
| DE | 198 05 690 | 8/1999 |
| EP | 0 850 910 | 7/1998 |
| WO | 03/051812 | 6/2003 |

OTHER PUBLICATIONS

International Search Report.
M. Schneider et al; "Industrial application of Nafion-systems in rearrangement-aromatisation, transesterification, alkylation, and ring-closure reactions"; vol. 220, No. 1-2; 2001; pp. 51-58.

* cited by examiner

*Primary Examiner*—Paul A. Zucker
(74) *Attorney, Agent, or Firm*—Nixon & Vanderhye P.C.

(57) ABSTRACT

2,3,5-Trimethyl-1,4-hydroquinone diacylates are obtained by reacting 3,5,5-trimethyl-1,4-benzoquinone with an acylating agent in the presence of methane trisulfonic acid as a catalyst.

9 Claims, No Drawings

PROCESS FOR THE PREPARATION OF 2,3,5-TRIMETHYLHYDROQUINONE DIACYLATES

This application is the US national phase of international application PCT/EP2004/01 2058 filed 26 Oct. 2004 which designated the U.S. and claims benefit of EP 03025513.7, dated 7 Nov. 2003, the entire content of which is hereby incorporated by reference.

The present invention is concerned with a process for the preparation of 2,3,5-trimethylhydroquinone diacylates by reacting 3,5,5-trimethyl-1,4-benzoquinone (ketoisophorone) with an acylating agent in the presence of methanetrisulfonic acid. 2,3,5-Trimethylhydroquinone diacylates are useful as reactants for the preparation of 2,3,5-trimethylhydroquinone, itself a valuable reactant for the preparation of (all-rac)-α-tocopherol.

2,3,5-Trimethylhydroquinone diacylates are known to be producible by reacting ketoisophorone with an acylating agent in the presence of a strongly acidic catalyst. Many such catalysts have been proposed in the past for this purpose, in particular protonic acids, e.g. such inorganic acids as sulphuric acid; such organic acids as p-toluenesulphonic acid; strongly acidic ion exchange resins; and such Lewis acids as zinc chloride, boron trifluoride, antimony pentafluoride and titanium tetrachloride: see inter alia German Offenlegungsschrift 2149159 and European Patent Publications EP 0916642 A1 and EP 1028103 A1; as well as NH-acidic or CH-acidic catalysts, see PCT Publication WO 03/051812.

It has now been found that by the use of small amounts of methanetrisulfonic acid, the conversion of ketoisophorone to 2,3,5-trimethylhydroquinone diacylates can be accomplished in high yield and without the need to use additional solvents. The use of methanetrisulfonic acid as the catalyst provides, all in all, advantages over catalysts used so far in this reaction in terms of stability of the catalyst, high yield, selectivity, and costs.

Thus, the presence invention relates to a process for the preparation of 2,3,5-trimethyl-1,4-hydroquinone diacylates by reacting 3,5,5-trimethyl-1,4-benzoquinone with an acylating agent in the presence of methane trisulfonic acid.

The acylating agent used in the process of the present invention may be any acylating agent that is conventionally used in the conversion of ketoisophorone to 2,3,5-trimethylhydroquinone acylates, particularly acid anhydrides, acyl halides, and enol esters. Examples of acid anhydrides are straight or branched chain alkanoic acid anhydrides such as acetic, propionic and butyric anhydride. Examples of acyl halides are straight or branched chain alkanoyl chlorides such as acetyl, propionyl and butyryl chloride. Finally, examples of enol esters are isopropenyl acetate and butyrate. The preferred acylating agent is acetic anhydride or acetyl chloride, especially acetic anhydride.

The process of the present invention can be carried out in the absence of a solvent. While the ratio of acylating agent to ketoisophorone is not narrowly critical the molar ratio of acylating agent to ketoisophorone is suitably from about 1:1 to about 10:1, preferably from about 5:1 to about 3:1, and is most preferably about 3:1.

The amount of catalyst, methane trisulfonic acid, is suitably about 0.01 to about 2.0 mole %, preferably about 0.075 to about 1.5 mole %, and most preferably about 0.1 to about 1.0 mole %, based on the amount of ketoisophorone.

The process is conveniently carried out at temperatures from about 0° C. to about 140° C., preferably from about 20° C. to about 90° C., especially 20° C. to 70° C.

The process according to the present invention may be carried out batchwise or in continuous mode. Moreover, the process is conveniently carried out under an inert gas atmosphere, preferably under gaseous nitrogen or argon.

The progress of the reaction is suitably monitored by gas chromatography and mass spectrometry of samples taken from the reaction mixture at various time intervals during the reaction.

The produced 2,3,5-trimethylhydroquinone diacylate can be isolated after distilling off the remaining acylating agent and the secondary product formed in the acylation, e.g. acetic acid when acetic anhydride is used as the acylating agent, by extraction of the crude product mixture with a suitable organic solvent, e.g. toluene. For instance, in effecting this procedure using acetic anhydride as the acylating agent 2,3,5-trimethylhydroquinone diacetate was obtained as colourless crystals after evaporating off the toluene used as the extracting solvent. Another isolation procedure is the crystallization of the 2,3,5-trimethylhydroquinone diacylate from the mixture at the termination of the reaction by cooling, and, optionally, adding water, to the mixture to promote the crystallization.

The catalyst can be recovered by extraction with water or acid-water and concentration of the extract. Alternatively, the catalyst can be recovered by adding a biphasic solvent system, e.g. a carbonate (particularly ethylene carbonate or propylene carbonate) and an aliphatic hydrocarbon (particularly heptane or octane), and isolating it from the polar (carbonate) phase The 2,3,5-trimethylhydroquinone diacylate obtained by the process of the present invention can be converted into 2,3,5-trimethylhydroquinone by transesterification, i.e. by treatment with an alcohol, e.g. an aliphatic alcohol such as isopropanol or n-butanol. Depending on the amounts of alcohol and catalyst and on the temperature in the reaction mixture, the transesterification yields the unesterified 2,3,5-trimethylhydroquinone and the ester formed as the further product. 2,3,5-Trimethylhydroquinone can be converted into (all-rac)-α-tocopherol by known procedures by reaction with isophytol, preferably in a biphasic solvent system, e.g. in a solvent system comprising a polar solvent such as ethylene or propylene carbonate, and a non-polar solvent, particularly an aliphatic hydrocarbon such as heptane, see, e.g. international application PCT/EP03/01556.

The invention is illustrated further by the following Examples.

EXAMPLE 1

A 50-ml four-necked flat-bottomed flask equipped with a thermometer, a glass-tube (Ø5 mm) for Ar-purge, a reflux condenser and a magnetic stirring bar was charged with methanetrisulfonic acid (see Table 1 below) and 10.324 g (66 mmol) of ketoisophorone. Within 2 min, acetic anhydride was added dropwise (see Table 1 below) under rapid stirring. During addition, the mixture turned dark yellow to finally dark brown and the internal temperature increased. After cooling to the desired reaction temperature that temperature was maintained by means of an oil bath. Samples were withdrawn and submitted to qualitative GC-analysis. After the reaction time (see Table 1 below), the reaction mixture was cooled to room temperature and the catalyst was deactivated by addition of 3.7 g (70 mmol) anhydrous sodium carbonate. The reaction mixture was concentrated by 40° C./10 mbar thereby distilling off acetic acid and unreacted anhydride. The crude product was analyzed by GC using squalane as internal standard. The results and reactions conditions are given in Table 1 below:

TABLE 1

| (Ac₂O) [mmol] | (SO₃H)₃CH [mg] | (SO₃H)₃CH [mol %] | T [° C.] | time [h] | conversion [%] | TMHQ-DA [%] |
|---|---|---|---|---|---|---|
| 200 | 171.2 | 1.0 | 25 | 4 | 97.2 | 91.8 |
| 333 | 171.2 | 1.0 | 25 | 4 | 99.3 | 91.1 |
| 666 | 171.2 | 1.0 | 25 | 4 | 99.2 | 94.0 |
| 200 | 93.5 | 0.55 | 25 | 22 | 78.6 | 69.0 |
| 200 | 171.2 | 1.0 | 25 | 22 | 100 | 96.6 |
| 200 | 342.4 | 2.0 | 25 | 22 | 100 | 93.2 |
| 200 | 120 | 0.7 | 60 | 4 | 99.1 | 91.5 |
| 200 | 120 | 0.7 | 60 | 4 | 99.3 | 92.9 |
| 200 | 120 | 0.7 | 60 | 4 | 98.9 | 92.3 |
| 200 | 34.2 | 0.2 | 70 | 4 | 83.5 | 72.2 |
| 200 | 94.2 | 0.55 | 70 | 4 | 100 | 92.6 |
| 200 | 154.1 | 0.9 | 70 | 4 | 100 | 94.2 |
| 200 | 171.2 | 1.0 | 40 | 4.5 | 98.8 | 88.2 |
| 200 | 342.4 | 2.0 | 40 | 3.5 | 100 | 90.0 |

The values given are averages from several measurements (two or three) and two experiments.

Ac₂O: acetic anhydride; TMHQ-DA: 2,3,5-trimethyl-1,4-hydroquinone diacetate [yield]

EXAMPLE 2

Using a 230 ml-flask the procedure of Example 1 was repeated with changing ratios of ketoisophorone and acetic anhydride. The reaction conditions and results are given in Table 2 below:

TABLE 2

| (Ac₂O) [mmol] | KIP/Ac₂O₃CH [ratio] | T [° C.] | time [h] | conversion [%] | TMHQ-DA [%] | S(TMHQ-DA) [%] |
|---|---|---|---|---|---|---|
| 299 | 1:2.25 | 45 | 12 | 89.7 | 85.8 | 95.6 |
| 332 | 1:2.5 | 45 | 12 | 91.9 | 87.2 | 94.9 |
| 398 | 1:3 | 45 | 12 | 95.6 | 90.9 | 95.1 |
| 663 | 1:5 | 45 | 12 | 98.6 | 94.5 | 95.8 |
| 1327 | 1:10 | 45 | 12 | 98.1 | 93.0 | 94.8 |
| 398 | 1:3 | 25 | 24 | 83.6 | 80.6 | 96.3 |

The values given are averages from several measurements (two or three) and two experiments. S: Selectivity.

EXAMPLE 3

In analogy to the procedure of Example 1, the reaction conditions were optimized using a statistical model (STAVEX). 20.32 g (200 mmol) of acetic anhydride were added within 10 min. to 10.324 g (66 mmol) of ketoisophorone. The results are tabulated in Table 3 below:

TABLE 3

| (SO₃H)₃CH [mg] | (SO₃H)₃CH [mmol] | (SO₃H)₃CH [mol %] | T [° C.] | time [h] | conversion [%] | TMHQ-DA [%] |
|---|---|---|---|---|---|---|
| 17.2 | 0.07 | 0.1 | 25 | 4 | 0 | 0 |
| 17.4 | 0.07 | 0.1 | 100 | 4 | 43.2 | 14.8 |
| 172.5 | 0.67 | 1.0 | 100 | 4 | 100 | 83.5 |
| 85.6 | 0.33 | 0.5 | 40 | 14 | 97.6 | 89.7 |
| 17.2 | 0.07 | 0.1 | 25 | 24 | 10.8 | 1.0 |
| 85.5 | 0.33 | 0.5 | 55 | 14 | 100 | 90.3 |
| 85.5 | 0.33 | 0.5 | 55 | 22 | 100 | 91.4 |
| 171.4 | 0.67 | 1.0 | 25 | 4 | 83.9 | 75.6 |
| 85.6 | 0.33 | 0.5 | 85 | 14 | 100 | 89.6 |
| 17.1 | 0.07 | 0.1 | 100 | 24 | 45.6 | 16.4 |
| 34.4 | 0.13 | 0.2 | 55 | 14 | 88.7 | 79.0 |
| 85.5 | 0.33 | 0.5 | 55 | 6 | 99.5 | 90.4 |
| 171.1 | 0.67 | 1.0 | 25 | 24 | 99.3 | 92.7 |
| 154.2 | 0.60 | 0.9 | 55 | 14 | 100 | 91.3 |
| 171.4 | 0.67 | 1.0 | 100 | 24 | 100 | 84.6 |
| 171.3 | 0.67 | 1.0 | 60 | 7 | 100 | 91.2 |

TABLE 3-continued

| (SO$_3$H)$_3$CH [mg] | (SO$_3$H)$_3$CH [mmol] | (SO$_3$H)$_3$CH [mol %] | T [° C.] | time [h] | conversion [%] | TMHQ-DA [%] |
|---|---|---|---|---|---|---|
| 128.1 | 0.50 | 0.8 | 60 | 10 | 100 | 91.9 |
| 85.5 | 0.33 | 0.5 | 60 | 12 | 100 | 93.5 |

EXAMPLE 4

Based on the results of Example 3, experiments under optimized conditions were carried out. The results are summarized in Table 4

TABLE 4

| (Ac$_2$O) [mmol] | KIP/Ac$_2$O ratio | (SO$_3$H)$_3$CH [mol %] | T [° C.] | time [h] | conversion [%] | TMHQ-DA [%] | S(TMHQ-DA) [%] |
|---|---|---|---|---|---|---|---|
| 398 | 1:3 | 0.5 | 60 | 6 | 97.4 | 92.0 | 94.5 |
| 663 | 1:5 | 1.0 | 25 | 24 | 100 | 96.7 | 96.7 |

What is claimed is:

1. Process for the preparation of 2,3-5-trimethyl-1,4-hydroquinone diacylates by reacting ketoisophorone with an acylating agent in the presence of methane trisulfonic acid.

2. A process as in claim 1 wherein the reaction is carried out in the presence of about 0.01 mol % to about 2 mol % of methane trisulfonic acid, based on ketoisophorone.

3. A process as in claim 2 wherein the reaction is carried out in the presence of about 0.1 mol % to about 1 mol % of methane trisulfonic acid, based on ketoisophorone.

4. A process as in claim 1 wherein the molar ratio of acylating agent to ketoisophorone is about 10 to 1.

5. A process as in claim 1 wherein the acylating agent is acetic anhydride.

6. A process as in claim 1 wherein the reaction is carried out at about 0° C. to about 140° C.

7. A process as in claim 1 wherein the 2,3,5-trimethyl-1,4-hydroquinone diester obtained is converted in a manner known per se to α-tocopherol.

8. A process as in claim 4 wherein the molar ratio is about 3 to 1.

9. A process as in claim 1 wherein the reaction is carried out at about 20° C. to about 70° C.

* * * * *